US006753035B2

(12) United States Patent
Laks et al.

(10) Patent No.: US 6,753,035 B2
(45) Date of Patent: Jun. 22, 2004

(54) COMPOSITIONS AND METHODS FOR WOOD PRESERVATION

(75) Inventors: Peter Laks, Hancock, MI (US); Patricia A. Heiden, Houghton, MI (US)

(73) Assignee: Board of Control of Michigan Technological University, Houghton, MI (US)

( * ) Notice: Subject to any disclaimer, the term of this patent is extended or adjusted under 35 U.S.C. 154(b) by 0 days.

(21) Appl. No.: 10/348,313

(22) Filed: Jan. 21, 2003

(65) Prior Publication Data

US 2003/0134137 A1 Jul. 17, 2003

Related U.S. Application Data

(62) Division of application No. 09/871,521, filed on May 31, 2001, now Pat. No. 6,521,288.
(60) Provisional application No. 60/208,249, filed on May 31, 2000.
(51) Int. Cl.[7] .................................................. B05D 3/12
(52) U.S. Cl. ...................... 427/180; 427/369; 427/393; 427/397
(58) Field of Search .............................. 427/180, 369, 427/393, 397

(56) References Cited

FOREIGN PATENT DOCUMENTS

| EP | 984966 | * 11/1999 |
| JP | 02-250801 | * 10/1990 |
| JP | 04-212804 | * 8/1992 |

OTHER PUBLICATIONS

Y. Liu, L. Yan, P. Heiden, and P. Laks; Use of Nanoparticles for the Controlled Release of Biocides in Pressure–Treated Solid Wood; Polymer Preprints 38(2), 1997, pp. 624–625.
Y. Liu, L. Lan, and P. Heiden; Use of Nanoparticles for the Controlled Release of Biocides in Pressure–Treated Solid Wood, Presentation at American Chemical Society, Las Vegas, Oct. 1997.
Y. Liu, L. Yan, P. Heiden, and P. Laks; Use of Nanoparticles for the Controlled Release of Biocides in Solid Wood; Journal of Applied Polymer Science, Jan. 2001 and Nov. 20, 2000; pp. 458–465.

* cited by examiner

Primary Examiner—Erma Cameron
(74) Attorney, Agent, or Firm—Michael Best & Friedrich LLP

(57) ABSTRACT

The invention provides a method for incorporating biocides into wood or a wood product. The method comprises incorporating an additive into a nanoparticle, applying the nanoparticle to wood or a wood particle and applying sufficient pressure to force the nanoparticle to penetrate the wood or wood particle.

18 Claims, 8 Drawing Sheets

Soil Block Results

Chlorothalonil PVPy/Sty Nanoparticles

Effect of Polymer Composition- *Trametes versicolor*

Polymer Composition (%Sty in PVPy)

CTL Retn (Kg/m3): 0, 0.5, 1, 2, 4

FIG. 4

Figure 13. Percent weight loss from a soil-block decay test of leached aspen waferboard manufactured with incorporation of three tebuconazole formulations(powder, solution and nanoparticles) at the different A.I. loadings after exposure to the fungi (*Trametes versicolor*) for 12 weeks.

Comparison of Surfactant and Surfactant-Free Nanoparticles

| Matrix/A.I./ Prep. | Avg. Diam. (nm) | Diam. Range (nm) | A.I. Content (%) | Max. Susp. Loading (mg/100 mL) |
|---|---|---|---|---|
| PVPy/TEB/S | 112 | 50 - 400 | 50 | 200 |
| PVPy/TEB/SF | 74 | 50 - 1000 | 50 | 500 - 600 |
| PVPy/CTL/S | 169 | 50 - 500 | 37 | 150 |
| PVPy/CTL/SF | ppt. | | | |
| PVPy-AA/CTL/SF | 123 | 50 - 2000 | 50 | ~300 |

S = Surfactant-based preparation method.
SF = Surfactant -free.
Ppt. = Precipitate

Fig. 8

COMPOSITIONS AND METHODS FOR WOOD PRESERVATION

CROSS-REFERENCE TO RELATED APPLICATIONS

This application is a divisional of application Ser. No. 09/871,521 filed May 31, 2001, which issued as U.S. Pat. No. 6,521,288 on Feb. 18, 2003 and claims priority under 35 U.S.C. §119 to provisional patent application No. 60/208,249 filed May 31, 2000.

BACKGROUND OF THE INVENTION

The production of wood which has been treated to inhibit biological decomposition is well known. The organisms causing wood decomposition include: basidiomycetes such as *Gloeophyllum trabeum* (brown rot), *Trametes versicolor* (white rot), *Serpula lacrymans* (dry rot) and *Coniophora puteana*; coleopterans such as *Anobium punctatum* (furniture beetle), *Hylotrupes bajulus* (house longhorn) and *Xestobium rufovillorum* (death watch beetle); and hyrnenopterans such as termites and carpenter ants. In 1996, 592 million cubic feet of pressure-treated wood was produced in the United States.

The major product of the industry is southern pine lumber treated with chromated copper arsenate (CCA). Most of this treated lumber is used for decks, fencing and landscape timbers. There is concern about the safety and health effects of CCA as a wood preservative. Alternative wood preservative systems for lumber, with lower perceived risk, such as ammoniacal copper quat (ACQ), copper bis (dimethyldithiocarbamate) (CDDC), ammoniacal copper citrate and copper azole, are also in limited commercial use.

Modern organic biocides are considered to be relatively environmentally benign and not expected to pose the problems associated with CCA-treated lumber. Biocides such as tebuconazole are quite soluble in common organic solvents while others such as chlorothalonil possess only low solubility. The solubility of organic biocides affects the markets for which the biocide-treated wood products are appropriate. Biocides with good solubility can be dissolved at high concentrations in a small amount of organic solvents, and that solution can be dispersed in water with appropriate emulsifiers to produce an aqueous emulsion. The emulsion can be used in conventional pressure treatments for lumber and wood treated in such a manner can be used in products such as decking where the treated wood will come into contact with humans. Biocides which possess low solubility must be incorporated into wood in a solution of a hydrocarbon oil such as AWPA P9 Type A and the resulting organic solution used to treat wood directly. Wood treated in this way can be used only for industrial applications, such as utility poles and railway ties, because the oil is irritating to human skin.

It would be desirable to find a means of applying a broad spectrum of organic biocides of varying solubility and activity to wood that avoids the use of irritating or toxic oils.

SUMMARY OF THE INVENTION

The invention provides a method for incorporating additives into wood or a wood product. The method comprises incorporating an additive into a nanoparticle, applying the nanoparticle to wood or a wood particle and applying sufficient pressure to force the nanoparticle to penetrate the wood or wood particle.

The invention further provides a method for incorporating additives into wood or a wood product. The method comprises incorporating a biocide into a nanoparticle, blending the nanoparticle into wood particles and applying sufficient pressure to form a wood product.

The invention further provides a method of inhibiting decomposition of wood or a wood product. The method comprises incorporating a biocide into a nanoparticle, applying the nanoparticle having the biocide incorporated therein to wood or a wood product and applying sufficient pressure to force the nanoparticle to penetrate the wood or wood particle.

The invention further provides a finished wood article or wood product comprising wood and a nanoparticle having a biocide incorporated therein. The nanoparticle is incorporated in the wood.

BRIEF DESCRIPTION OF THE DRAWINGS

FIG. 4 shows the preservation of pine with PVPy/Sty (heteropolymer)/CTL nanoparticles.

FIG. 8 shows a comparison of surfactant and surfactant-free nanoparticles.

Figure 1:
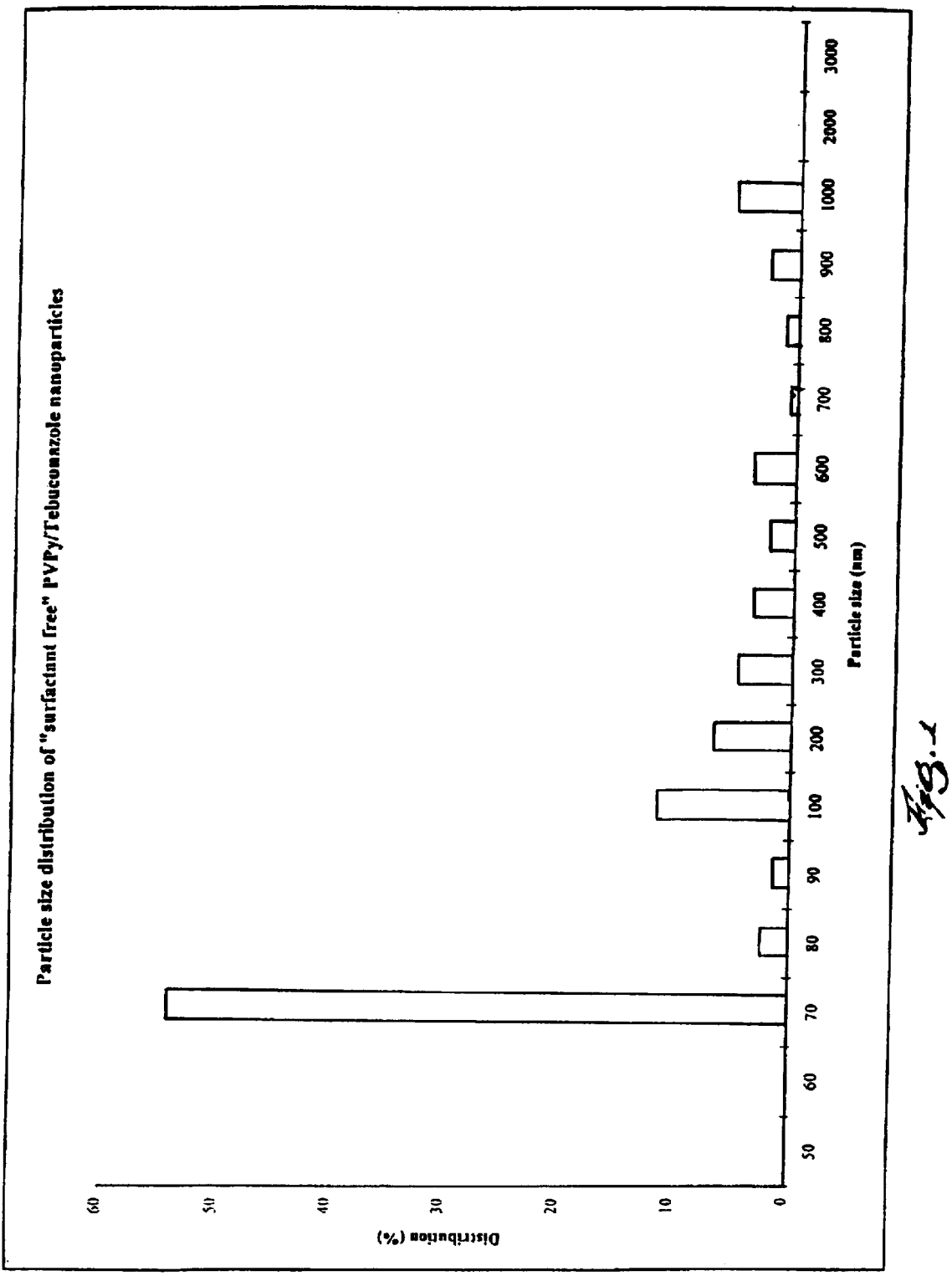
FIG. 1 shows the size distribution of PVPy/Tebuconazole nanoparticles.
Figure 2:
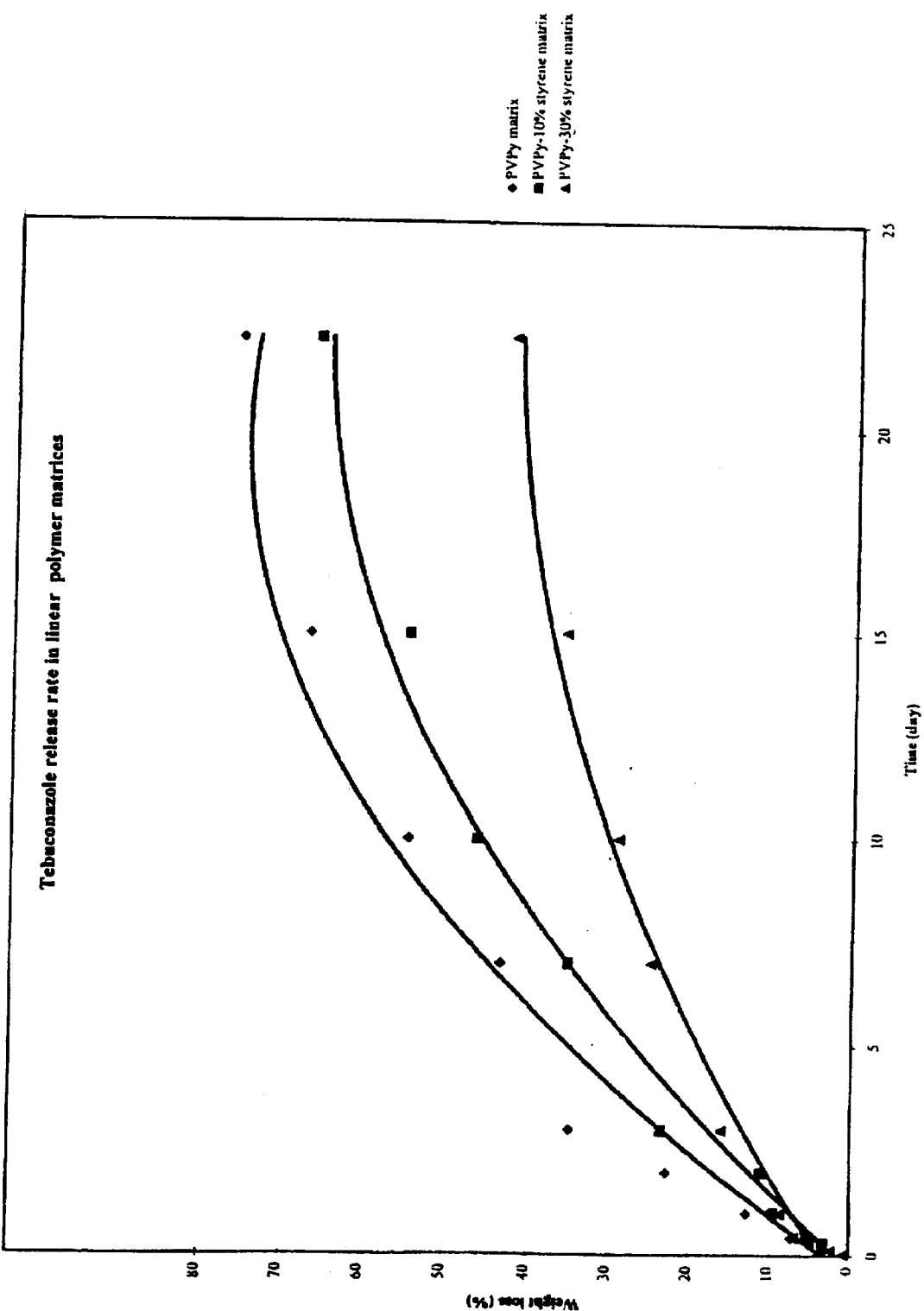
FIG. 2 shows the release rates of TEB from three different matrices.
Figure 3:
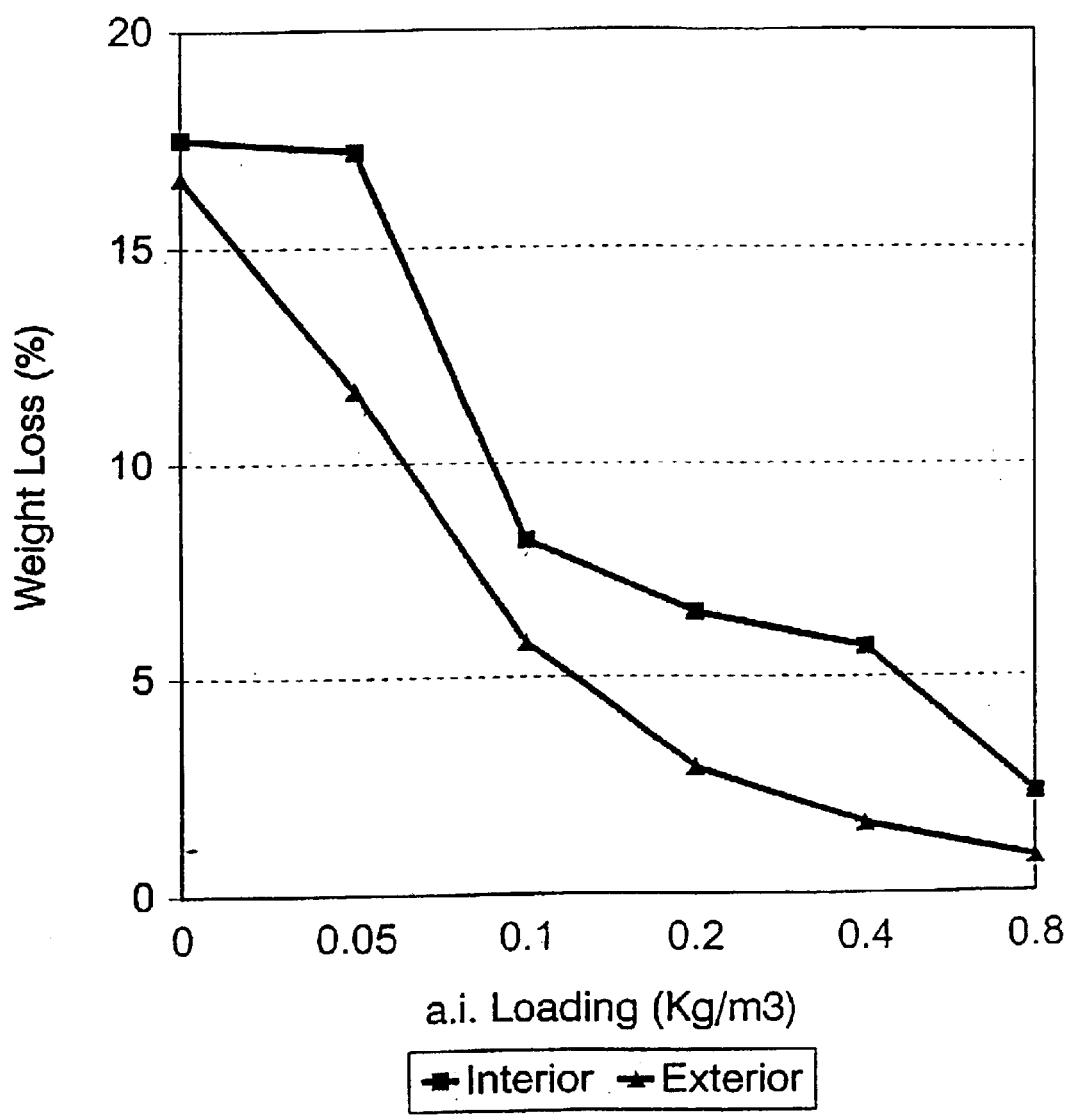
FIG. 3 shows the preservation of pine with TEB/PVPy Nanoparticles.
Figure 5:
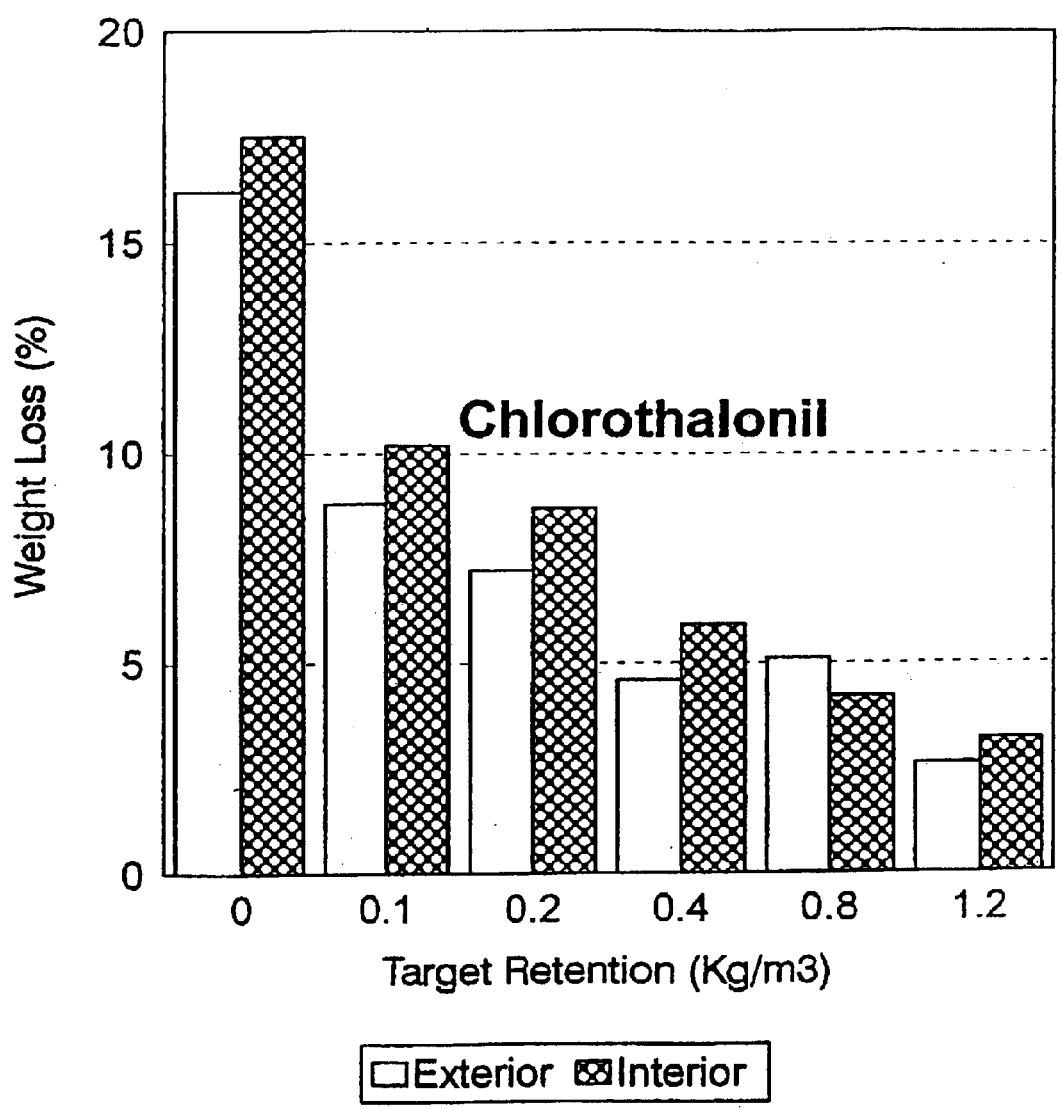
FIG. 5 shows the preservation of pine with CTL nanoparticles.
Figure 6:
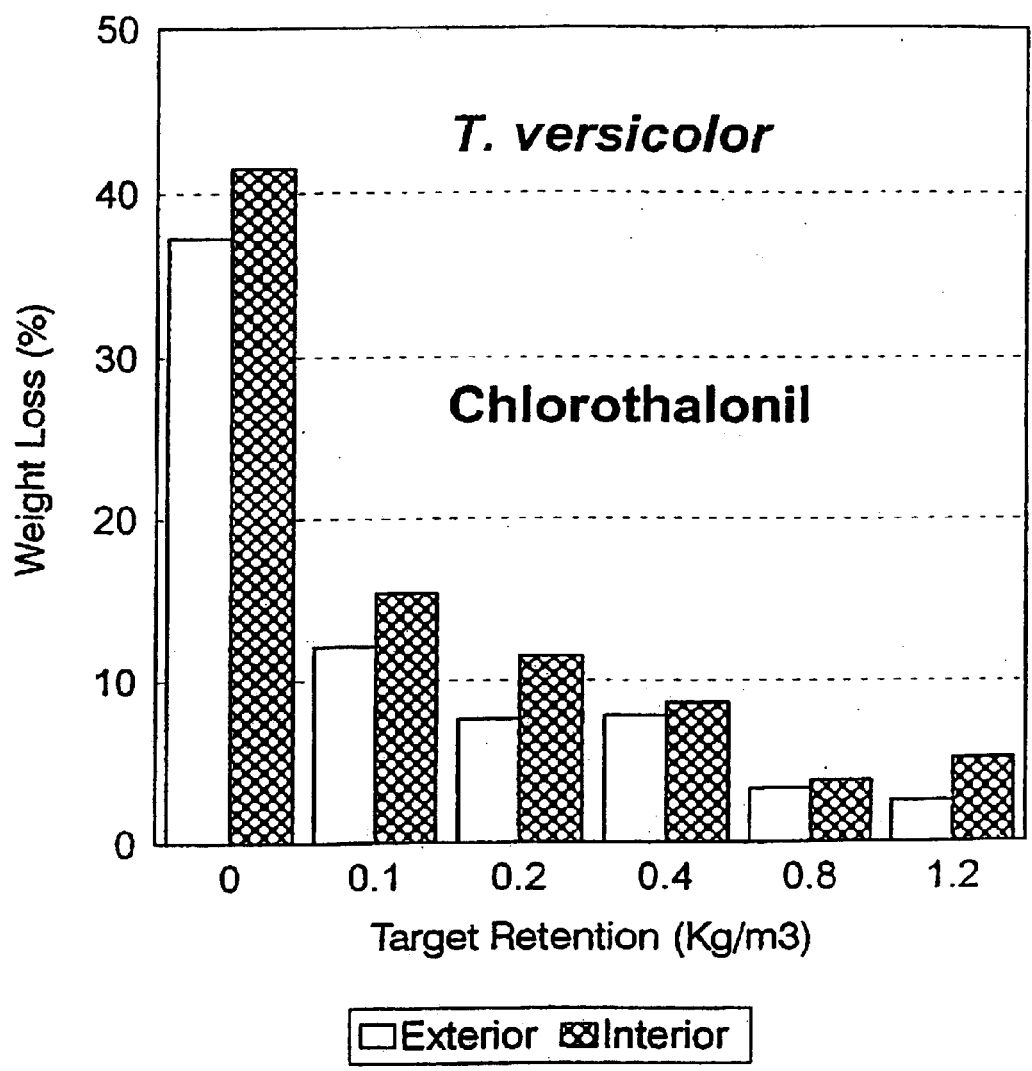
FIG. 6 shows the preservation of birch with CTL nanoparticles.

The invention is herein described in the form of certain preferred embodiments, which should be considered representative only. It is to be understood that those skilled in the art may make many variations, modifications and substitutions without falling outside the scope and spirit of this invention. All such variations, modifications and substitutions are considered to be with the scope of the claims to this invention.

DETAILED DESCRIPTION OF THE INVENTION

It is well known in the art that it is possible to make particles of polymers which incorporate solutes present during polymerization. Surprisingly, it is shown that nanoparticles of a certain size range can be made to penetrate wood, using pressure treatments standard in the industry. An additional benefit is provided in that the porosity of the polymer can be readily adjusted so as to control the rate of release of the incorporated solutes. The absence of surface active agents gives even finer control over the rate of release of the solute. This fine-tuned rate of release of biocides is advantageous in the manufacture of pressure-treated wood products and wood composites such as oriented strand board (OSB), particle board (PB), medium density fiberboard (MDF), plywood, laminated veneer lumber (LVL), laminated strand lumber (LSL), hardboard and the like, in which case the nanoparticle suspension or dry powder can be blended with the wood particles or mixed with the adhesive or water repellent to produce a treated wood composite. These nanoparticles contain no surfactant to interfere with the bonding or to make the wood composite hydrophilic.

This invention discloses compositions and methods for incorporating biocides active against the organisms causing wood decomposition into nanoparticles that are made of a size can be pressure-forced into wood or incorporated into wood composites. These nanoparticles can be made from many polymers and the porosity varied so as to yield various degrees of porosity, that is, to control the rate at which the trapped solute will diffuse from the particle. Several advantages are realized by incorporating organic biocides into polymeric nanoparticles and introducing the nanoparticles into wood composites. Since the biocides are dispersed in a solid, insoluble polymeric nanoparticle which can be suspended in water or any convenient liquid or simply used as a dry powder, any biocide, even those with low solubility in organic solvents, can be introduced into wood using the conventional pressure treatment techniques now used for water-borne biocides. In addition, the polymer component also acts as a diluent, so that a more even volumetric distribution of the biocide is achieved than, as in the prior art, incorporating small particles of the biocide into the wood or wood composite. In composite manufacture, the nanoparticle helps stabilize the biocide(s) during processing and reduces mutual negative interactions between the biocide(s) and adhesive.

Using the compositions and methods of this invention, low-solubility biocides can be used in wood products marketed for household applications, or any other use. Such biocide nanoparticles function as a storage reservoir for the biocide, controlling the release rate of the biocide according to the degree of porosity and also protecting the unreleased biocide from the environment and/or damaging process conditions. Since the biocide is afforded protection from random degradative processes until it is released, long-term protection is afforded to the wood.

The polymer to be used is selected based on (1) compatibility with the biocide(s) to be applied; (2) solubility characteristics, preferably high solubility of the polymer in organic solvents coupled with very low solubility of the polymer in water, (3) porosity suitable to the desired release rate of biocide(s); (4) ease of manufacture of particles of the desired size; and (5) effect of the stability on "stickiness," that is, the tendency to aggregate, of the resultant nanoparticles. In general, branched polymers tend to form less dense and more porous polymers than with higher biocide release rates than linear polymers. The polymers that are the preferred embodiments include but are not limited to: polyvinylpyridine, polymethacrylate, polystyrene, polyvinylpyridine/styrene copolymers, polyesters, polyethylene, polypropylene, polyvinylchloride, blends of the above homopolymers with acrylic acid and the like. Combinations of the above polymers are also suitable for use in the invention.

The biocide is chosen according to (1) the target organism; (2) solubility characteristics, that is, high solubility in the particle-forming solvent; (3) stability to the temperature and pH used to polymerize the monomer of choice; and other conditions found in the manufacture of wood composites. Biocides include any substance that kills or inhibits the growth of microorganisms such as molds, slimes, fungi, etc. Insecticides, fungicides and bactericides are all examples of biocides. Fungicides include any substance which kills or inhibits the growth of fungi. Bactericides include any agent that will kill bacteria. More specific examples of biocides include, but are not limited to, chlorinated hydrocarbons, organometallics, halogen-releasing compounds, metallic salts, organic sulfur compounds, compounds and phenolics. The biocides that are the preferred embodiments include but are not limited to: copper naphthenate, zinc naphthenate, quaternary ammonium salts, pentachlorophenol, tebuconazole (TEB), chlorothalonil (CTL), chlorpyrifos, isothiazolones, propiconazole, other triazoles, pyrethroids, and other insecticides, imidichloprid, oxine copper and the like. In addition to the above organic biocides, the methods of this invention may readily be used to produce nanoparticles with variable release rates that incorporate such inorganic preservatives as boric acid, sodium borate salts, zinc borate, copper salts and zinc salts. Any combination of two or more of the above biocides is suitable for use with the present invention.

Following the teaching of this invention, those skilled in the art may readily perceive that the compositions and methods within the scope of this invention as claimed are not limited to the biocides of the disclosed embodiments. For example, it is desirable to treat wood and wood products with fire retarding chemicals such as borax/boric acid, guanylurea phosphate-boric acid, dicyandiamide phosphoric acid formaldehyde and diethyl-N,N-bis(2-hydroxyethyl) aminomethyl phosphate. These fire retardants are most readily incorporated into nanoparticles formed from polyvinylpyridine or polyvinylchloride. Other additives that are confer desirable characteristics on wood and wood products and which are also within the scope of this invention are water repellants, colorants, UV inhibitors and adhesive catalysts.

EXAMPLE 1

Preparation of Polymeric Nanoparticles
A. Nanoparticles Prepared with Surfactant.

Nanoparticles were prepared in the presence of one biocide. Tebuconazole (Miles, Inc., Milwaukee) was dissolved in a small amount of methanol while chlorothalonil (ISK Biosciences, Memphis, Tenn.) was dissolved in a small amount of N-methylpyrrolidone. Each individually was added to a solution of PVPy in methanol or PVPy-coSty in N-methylpyrrolidone. The combined solution was dripped slowly into warm water (60° C.) containing a surfactant mixture of Tween 80 and Span 80 and stirred at 400–500 rpm for 30 minutes. The ratio of Tween 80 to Span 80 is varied to control the HLB(hydrophile/lipophile balance) number. HLB numbers of 9–11 gave optimal results. The resulting nanoparticle suspension was subjected to centrifugation (20,000 rpm for 20 minutes) and the liquid decanted. The solid was resuspended in water and freeze-dried to obtain dry nanoparticles.

B. Preparation of V50-Initiated Pvpy Surfactant-Free Tebuconazole Nanoparticles.

4-Vinylpyridine (5.85 g, 40 mmol) and methanol (100 ml) were charged into a 250 ml round-bottom flask. The solution was purged with nitrogen, then heated to boiling. V50 (1.2 mmol) was dissolved in methanol (20 ml) and added to the reaction solution over 10 minutes. Following the addition, the solution was allowed to cool, and the reaction continued overnight. All solvent and unreacted monomer were removed under reduced pressure. The yield was 88% and the Mn was 43,000 g/mol. The polymer was used to make tebuconazole-containing nanoparticles by the same general method described in Example 1A, except that no surfactant was present in the water phase.

C. Preparation of V50-Initiated Pvpy-Co-Acrylic Acid Chlorothalamil Nanoparticles.

The polymer synthesis procedure of Example 1B was followed, except that acrylic acid)AA_(0.1 g, 0.8 mmol, 2% with respect to vinylpyridine) was added to the vinylpyridine reaction mixture. The yield was 89% and the Mn was 41,000 g/mol. The polymer was used to make chlorothalanil-containing nanoparticles by the same general method described in Example 1A, except that no surfactant was present in the water phase. The nanoparticle yield was 86% and the chlorothalonil content was 95% of theoretical.

D. PVPy/HBP Nanoparticles.

Solutions of PVPy (10 mg in 2 ml of methanol) and HBP (g2, g3, g4, or g5, 10 mg) in a minimum amount of acetone were combined and placed in an addition funnel. The procedure described in Example 1A was then followed using either tebuconazole or chlorthalonil. These nanoparticles had varying degrees of porosity and polarity due to the blend of hyperbranched polyester with PVPy. The nanoparticle yield was 75–88%. The biocide content in the nanoparticles was 96–100% of theoretical for tebuconazole and 90–92% of theoretical for chlorothalanil.

E. Other Nanoparticles.

It is well known to those skilled in the art that polymeric nanoparticles can be made. For example, polystyrene nanoparticles can be made by pouring carboxylated polystyrene into water while stirring rapidly. Pre-made poly-(D,L-lactide) has been made by dissolving the polymer in acetone and then dripping the solution into an aqueous surfactant mixture with rigorous stirring. Polyalkylcyanoacrylate nanoparticles have been prepared by adding the cyanoacrylate monomer to surfactant-containing water to make micelles in the nanometer range, and then adding a catalyst to initiate the polymerization of the monomer to make the final nanoparticle product.

F. Measurements of Nanoparticle Density and Size.

A known mass of nanoparticles (1.0000 to 2.0000 g) was placed in a 10.0 ml graduated cylinder along with 8.0 ml of silicone oil and allowed to stand for fifteen minutes. The density of the nanoparticles was determined as the mass of nanoparticles over the change in volume. Density measurements were the average of three measurements and were reproducible with an accuracy of +/−0.1 cm$^3$ The size and dispersity of nanoparticles was measured by particle sizing (Shimadzu CP4, centrifugal force). Table I is a summary of the results. FIG. 1 shows the size distribution of PVPy/TEB nanoparticles while Table II illustrates the comparison between surfactant containing and surfactant-free nanoparticles.

EXAMPLE 2

Preservation of Wood by Nanoparticles Containing Biocides

Wood block specimens (19 $mm^3$ cubes) were weighed and accurately measured. Blocks were placed in beakers, covered with a mesh screen, weighted down, and a nanoparticle suspension to be tested was poured over the wood block. The beaker was then placed in a pressurized cylinder and subjected to a pressure treatment consisting of a partial vacuum of 17.3 kPa for 25 minutes, followed by pressurization at 790 kPa for 45 minutes. Specimens were removed, excess liquid wiped off, and weighed to determine the mass of suspension retained. The samples were then dried overnight in an oven at 40° C.

A variety of pressure treatments known in the art can be used to force the nanoparticles having the biocides incorporated therein to penetrate the wood or wood particles. For example, the nanoparticle suspension can be poured over wood and then pressurized in a pressurizable cylinder, e.g. a cylinder eight feet in diameter and sixty feet in length. Subsequently, a vacuum can be created to pull air out of the wood, followed by subsequent pressurization. Excess solution emanating from the wood can then be removed to yield a final wood product. Variations of pressure treating processes known to those of ordinary skill in the art are suitable for use with the current invention.

Nanoparticle-treated wood specimens were evaluated for fungal resistance in two ways. In the first method, the wood blocks were cut longitudinally into four wafers, two interior and two exterior and re-weighed. The blocks were sterilized in an autoclave for 15 minutes at 120° C. Using forceps, sterile toothpicks were placed on agar plates inoculated with the organism to be tested (*Gloeophyllurn trabeum* or *Trametes versicolor*) and the coded wafer sections were then placed directly on the toothpicks. Untreated wafers were similarly placed in each agar dish as control. The petri dishes were sealed with paraffin and incubated at 80° F. and 80% relative humidity. Following selected time of exposure, the wafers were harvested, cleaned, dried and re-weighed to determine the mass loss for test wafers, both interior and exterior sections and for controls.

FIGS. 3, 5 and 6 summarize the protection of pine and birch against degradation caused by exposure to *T. versicolor*. In each case, the pine lost about 17% of its weight at 0 biocide, while biocide ingredient at a loading of 0.1 $Kg/m^3$ reduced the loss to less than half that level while a loading of 0.8 $Kg/m^3$ virtually eliminated decay (FIGS. 3, TEB and 5, CTL). Birch lost more weight in the control sample than did pine. However, CTL nanoparticles reduced weight loss by 60% at a concentration of 0.1 $Kg/m^3$, and virtually eliminated loss at 0.8 Kg/m3 (FIG. 6). All of these results show that the nanoparticles have penetrated the wood, since the interior sections show the same profile as the exterior sections.

EXAMPLE 3

Incorporation of Nanoparticles Containing AI into Wood Composites

Wood composites can be made in a number of ways, depending on the size of the wood particles being used and the desired characteristics of the final product. Generally, the desired wood fibers, sawdust, wafers, strands or other particles are passed through a rotary blending device where the particles are tumbled while the adhesive, wax and any other additive are sprayed onto the particles. The blended particles are then formed into a loose collection that is pressed to cure the adhesive and form the composite pressure. The nanoparticles of this invention can be added to the particles at any point in the process, but most conveniently are added to the particles in the blender by spraying a nanoparticle suspension or metering the dried 20 powdered nanoparticles into the blender.

Aspen, *Populus tremuloides* Michx, wafers were generated to a target size of 2.2, 0.7, and 0.022 inches in length, width and thickness, respectively, with a six-foot Muller-Brugg disc flaker from clear, green, bark-free blocks. Wafers were dried until the moisture content reached 3 to 4 percent and then screened using a Black Clawson classifier with a ¼ inch vibration mesh to remove fines. Liquid polymeric diphenylmethane diisocyanate (pMMDI) resin, 100 percent solid content, was used to bond waferboard at a loading level of five percent based on oven-dry wafer weight. One percent of Wax was also added to increase water resistance. TEB was added in three different forms: as a TEB/PVPY nanoparticles suspension; a TEB/ethanol solution, and technical grade TEB powder. The target AI loadings of the TEB were 0.005, 0.01, 0.02, 0.04 and 0.08 pcf.

The wet components and wax were mixed by spraying in a rotary drum blender, while the powder TEB was just applied to the wafers. Mat moisture content was adjusted to eight percent with water prior to blending the additives and wafers. The order for all additives was water, TEB, wax and pMDI resin. Wafer mats were formed by hand, applying the blended furnish on a stainless steel caul plate under a deckle box. A release agent was sprayed on the caul to reduce risk of sticking prior to forming. Mats were pressed at a platen temperature of 400° F. for 180 seconds, including 30 seconds press closing time. After pressing, the panels were cooled to room temperature, trimmed into 16.5 by 6.5 inch panels and conditioned at 68+/−6° F. and 50% relative humidity.

Soil block tests were performed essentially as described in Example 2. The blocks were exposed to *T. versicolor* for 12 weeks at a temperature of 86° F. Decay was measured as percent weight loss of dried test samples.

Figure 7:
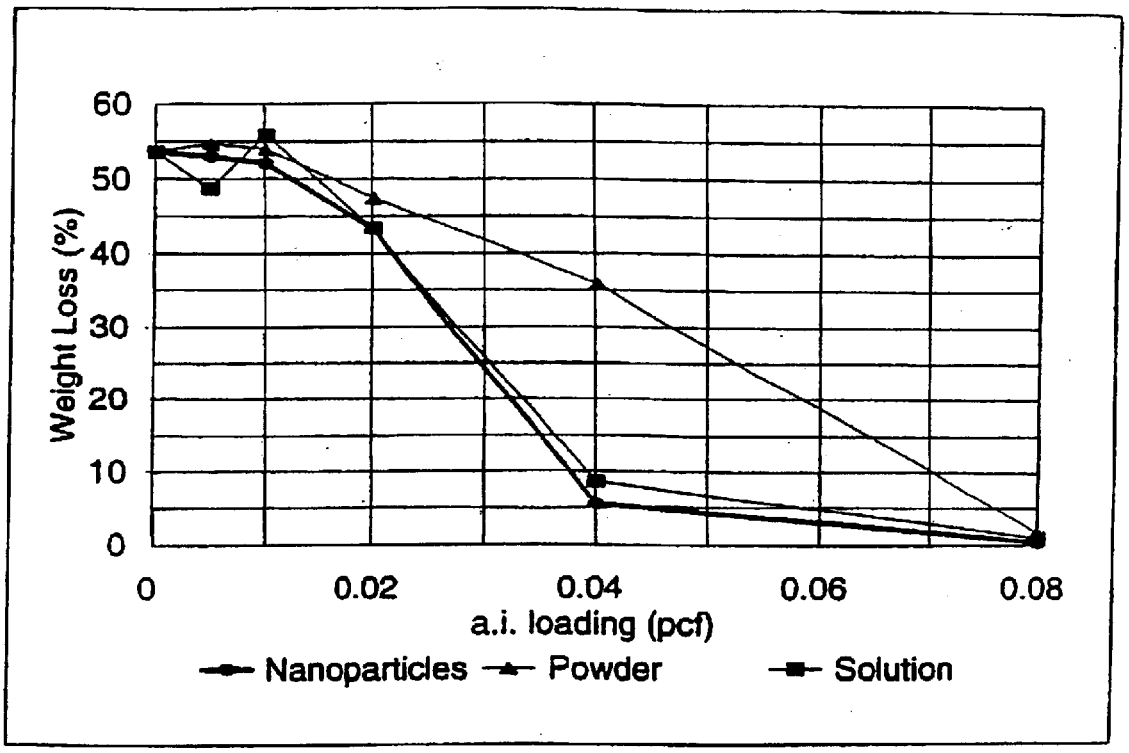
FIG. 7 shows the comparison of TEB applied as powder, nanoparticles or solution, into leached aspen wafer board.

As shown in FIG. 7, when nanoparticles containing TEB are incorporated into leached aspen waferboard, the results are similar to those obtained with TEB solution or powder, within the time frame investigated. However, it is to be expected that longer term protection with the nanoparticles will be seen when the time is extended beyond 12 weeks for two reasons. The rate of leaching is controllable with nanoparticles so the biocide will be present for a longer period and, additionally, the biocide will be protected within the polymer from environmental degradation.

We claim:

1. A method for incorporating additives into wood or a wood product, the method comprising:

synthesizing a nanoparticle having an additive incorporated therein without using a surfactant;

applying the nanoparticle to wood or a wood particle; and applying sufficient pressure to force the nanoparticle to penetrate the wood or wood product.

2. The method of claim 1, wherein the additive comprises a biocide.

3. The method of claim wherein the biocide comprises at least one of a quaternary ammonium salt, pentachlorophenol, chlorothalonil (CTL), chlorpyrifos, an isothiazolone, a pyrethroid, an insecticide, imidichloprid, oxine copper and a combination thereof.

4. The method of claim 2, wherein the biocide comprises at least one of boric acid, a sodium borate salt, zinc borate and a combination thereof.

5. The method of claim wherein the biocide comprises a fungicide.

6. The method of claim 5, wherein the fungicide comprises at least one of tebuconazole (TEB), propiconazole, a triazole and a combination thereof.

7. The method of claim 2, wherein the biocide comprises a metallic salt.

8. The method of claim wherein the metallic salt comprises copper naphthenate, zinc naphthenate, a zinc salt, a copper salt and a combination thereof.

9. The method of claim 2, wherein the nanoparticle is made from a polymer comprising at least one of polyvinylpyridine, polymethacrylate, polystyrene, a polyvinylpyridine/styrene copolymer, a polyester, polyethylene, polypropylene, polyvinylchloride, a combination thereof and a blend thereof with acrylic acid.

10. The method of claim 2, wherein the wood or wood product comprises at least one of oriented strand board (OSB), particle board (PB), medium density fiberboard (MDF), plywood, laminated veneer lumber (LVL), laminated strand lumber (LSL) and handboard.

11. A method of inhibiting decomposition of wood or a wood product, the method comprising:

using a polymer to incorporate a biocide into a nanoparticle, the polymer being modified in such a way that a surfactant is substantially not needed to incorporate the biocide into the nanoparticle;

applying the nanoparticle having the biocide incorporated therein to wood or a wood product; and applying sufficient pressure to force the nanoparticle to penetrate the wood wood particle.

12. The method of claim 11, where in the biocide comprises at least one of copper naphthenate, zinc naphthenate, a quaternary ammonium salt, pentachlorophenol, a zinc salt, tebuconazole (TEB), chlorothalonil (CTL), chlorpyrifos, an isothiazolone, propiconazole, a triazole, a pyrethroid, an insecticide, imidichloprid, oxine copper and a combination thereof.

13. The method of claim 11, wherein the biocide comprises at least one of boric acid, a sodium borate salt, zinc borate, a copper salt and a combination thereof.

14. The method of claim 11, wherein the nanoparticle is made from a polymer selected from the group consisting of polyvinylpyridine, polymethacrylate, polystyrene, polyvinylpyridine/styrene copolymer, polyester, polyethylene, polypropylene, polyvinylchloride, a combination thereof and a blend thereof with acrylic acid.

15. The method of claim 11, wherein the wood or wood product comprises at least one of oriented strand board (OSB), particle board (PB), medium density fiberboard (MDF), plywood, laminated veneer lumber (LVL), laminated strand lumber (LSL), handboard and a combination thereof.

16. A method for incorporating a biocide into wood or a product, the method comprising:

incorporating a biocide into a nanoparticle, the biocide selected from the group consisting of at least one of a quaternary ammonium salt, pentachlorophenol, chlorpyrifos, an isothiazolone, a pyrethroid, an insecticide, imidichloprid, oxine copper, boric acid, a sodium borate salt, zinc borate, propiconazole, a triazole, copper naphthenate, zinc naphthenate, zinc salt, copper salt and a combination thereof;

applying the nanoparticle to wood or a wood particle; and applying sufficient pressure to force the nanoparticle to penetrate the wood or wood particle.

17. A method for incorporating additives into wood or a wood product, the method comprising:

incorporating a biocide into a nanoparticle using a polymer, the polymer selected from the group consisting of at least one of polymethacrylate, polystyrene, polyester, polyethylene, polypropylene, polyvinylchloride, a combination thereof and a blend thereof with acrylic acid;

applying the nanoparticle to wood or a wood particle; and applying sufficient pressure to force the nanoparticle to penetrate the wood or wood particle.

18. A method for incorporating additives into wood, the method comprising:

synthesizing a nanoparticle having a biocide incorporated therein, with the proviso that the biocide is not tebuconazole or chlorothalonil;

applying the nanoparticle to wood; and applying sufficient pressure to force the nanoparticle to penetrate the wood.

* * * * *

INTER PARTES REEXAMINATION CERTIFICATE (491st)

United States Patent
Laks et al.

(10) Number: US 6,753,035 C1
(45) Certificate Issued: Dec. 12, 2012

(54) COMPOSITIONS AND METHODS FOR WOOD PRESERVATION

(75) Inventors: Peter Laks, Hancock, MI (US); Patricia A. Heiden, Houghton, MI (US)

(73) Assignee: Board of Control of Michigan Technological University, Houghton, MI (US)

Reexamination Request:
No. 95/000,206, Dec. 13, 2006

Reexamination Certificate for:
Patent No.: 6,753,035
Issued: Jun. 22, 2004
Appl. No.: 10/348,313
Filed: Jan. 21, 2003

Related U.S. Application Data

(62) Division of application No. 09/871,521, filed on May 31, 2001, now Pat. No. 6,521,288.

(60) Provisional application No. 60/208,249, filed on May 31, 2000.

(51) Int. Cl.
*B05D 3/12* (2006.01)

(52) U.S. Cl. .......... 427/180; 427/369; 427/393; 427/397

(58) Field of Classification Search .................. None
See application file for complete search history.

(56) References Cited

To view the complete listing of prior art documents cited during the proceeding for Reexamination Control Number 95/000,206, please refer to the USPTO's public Patent Application Information Retrieval (PAIR) system under the Display References tab.

*Primary Examiner* — Kiley Stoner

(57) ABSTRACT

The invention provides a method for incorporating biocides into wood or a wood product. The method comprises incorporating an additive into a nanoparticle, applying the nanoparticle to wood or a wood particle and applying sufficient pressure to force the nanoparticle to penetrate the wood or wood particle.

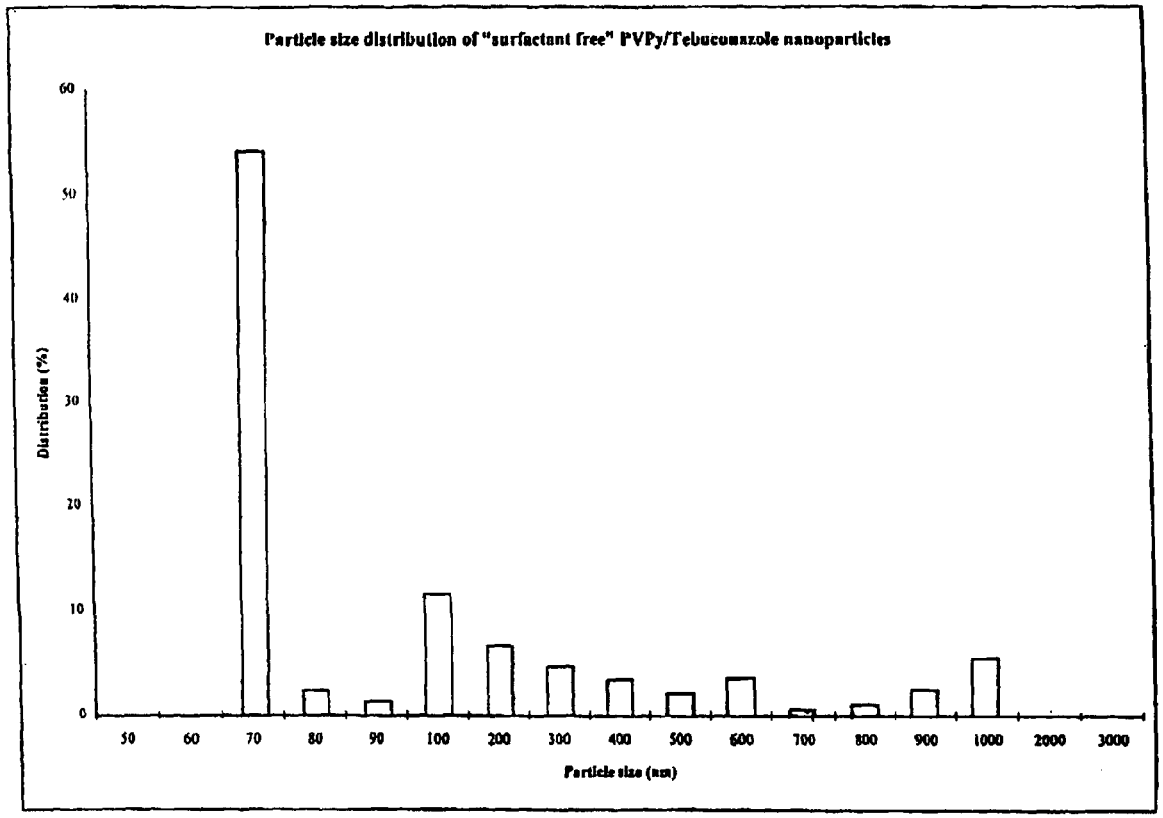

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-18 are cancelled.

\* \* \* \* \*